(12) United States Patent
Culton

(10) Patent No.: US 6,386,196 B1
(45) Date of Patent: May 14, 2002

(54) WARNING DEVICE FOR OXYGEN DELIVERY SYSTEM FAILURE

(76) Inventor: Steven E. Culton, 841 Sun River Ct., Paradise, CA (US) 95969

( * ) Notice: Subject to any disclaimer, the term of this patent is extended or adjusted under 35 U.S.C. 154(b) by 0 days.

(21) Appl. No.: 09/664,445

(22) Filed: Sep. 18, 2000

Related U.S. Application Data

(60) Provisional application No. 60/188,686, filed on Mar. 13, 2000.

(51) Int. Cl.[7] .................................................. A62B 9/00
(52) U.S. Cl. .......................... 128/205.23; 128/202.22; 116/137 R; 116/264; 116/273
(58) Field of Search ....................... 128/202.22, 202.27, 128/204.18, 204.23, 205.23, 205.24; 116/137 R, 142 FP, 70, DIG. 7, 2, 112, 264, 266, 268, 273, 274

(56) References Cited

U.S. PATENT DOCUMENTS

| | | | |
|---|---|---|---|
| 440,713 A | * 11/1890 | Krohne et al. ......... | 128/205.23 |
| 2,638,096 A | * 5/1953 | Waldhaus ............... | 116/137 R |
| 3,185,128 A | 5/1965 | Moore et al. | |
| 3,595,228 A | * 7/1971 | Simon et al. .......... | 128/202.22 |
| 3,814,091 A | * 6/1974 | Henkin .................. | 128/202.22 |
| 3,952,740 A | 4/1976 | Scurlock | |
| 4,011,828 A | 3/1977 | Black | |
| 4,067,329 A | * 1/1978 | Winicki ................. | 128/202.22 |
| 4,098,271 A | * 7/1978 | Maddock ............... | 128/202.22 |
| 4,188,946 A | * 2/1980 | Watson et al. ......... | 128/202.22 |
| 4,215,646 A | 8/1980 | Williams | |
| 4,350,115 A | 9/1982 | Pasternack | |
| 4,350,647 A | 9/1982 | De La Cruz | |
| 4,487,155 A | 12/1984 | Olesen | |
| 4,669,415 A | * 6/1987 | Boord .................... | 116/70 |
| 4,745,877 A | 5/1988 | Chang | |
| 4,793,190 A | 12/1988 | Chang | |
| 4,819,577 A | * 4/1989 | Campau ................. | 116/264 |
| 4,825,802 A | 5/1989 | Le Bec | |
| 5,057,822 A | 10/1991 | Hoffman | |
| 5,116,088 A | * 5/1992 | Bird ...................... | 128/202.27 |
| 5,293,866 A | 3/1994 | Padula | |
| 5,320,092 A | * 6/1994 | Ryder .................... | 128/202.22 |
| 5,322,059 A | * 6/1994 | Walther ................. | 128/205.23 |
| 5,522,380 A | * 6/1996 | Dwork ................... | 128/200.23 |
| 5,626,129 A | * 5/1997 | Klimm et al. ......... | 128/202.22 |
| 5,645,011 A | * 7/1997 | Winkler et al. ........ | 116/264 |
| 5,782,233 A | * 7/1998 | Niemi et al. ........... | 128/202.22 |
| 5,787,882 A | * 8/1998 | Hamilton ............... | 128/204.26 |
| 5,865,174 A | 2/1999 | Kloeppel | |
| 4,215,646 C1 | 10/1999 | Williams | |
| 6,186,744 B1 | * 2/2001 | Wolochuk .............. | 417/44.2 |

FOREIGN PATENT DOCUMENTS

| | | |
|---|---|---|
| GB | 729660 | 5/1955 |
| GB | 765847 | 1/1957 |

* cited by examiner

*Primary Examiner*—John G. Weiss
*Assistant Examiner*—Mital Patel
(74) *Attorney, Agent, or Firm*—Richard C. Litman

(57) ABSTRACT

An oxygen delivery system which provides a visual and audible warning signal for system or oxygen flow failure. When pressure fitted tubing detaches, the audible whistle alarm indicates that the oxygen delivery system has become disconnected and the system has failed. An audible alarm signals that the oxygen delivery system has failed. A clear acrylic ball, located at the device's central area, contains a fan. The fan is mounted so that it turns in response to oxygen flow. The turning fan has blades which are color coded to visually indicate the delivery rate of oxygen to a patient. An anti-reflux mechanism, located at the proximal end of the device assures the elimination of back-flow pathogens into re-usable permanent equipment.

3 Claims, 6 Drawing Sheets

WARNING DEVICE FOR OXYGEN DELIVERY SYSTEM FAILURE

CROSS-REFERENCE TO RELATED APPLICATION

This application claims the benefit of U.S. Provisional Patent Application Serial No. 60/188,686, filed Mar. 13, 2000.

BACKGROUND OF THE INVENTION

1. Field of the Invention

The present invention relates generally to a warning device for oxygen delivery system failure. More specifically, the device visually confirms the flow of oxygen delivery, and audibly alerts medical personnel, via a whistling sound, should the device become disconnected from an oxygen source.

2. Background of the Invention and Description of Related Art

Man can endure a month without food, survive a week without water, but deprive him of oxygen, and he dies in mere minutes. Thankfully, healthy individuals get all the oxygen they need from the surrounding atmosphere. Less fortunate folk must rely on oxygen delivery systems to keep them alive.

Tragically, oxygen delivery systems fail, and people die. Disconnected tubing is a common cause of system failure. The coupler that joins the oxygen source and the patient's tubing easily disconnects. This is by design. Without a weak point for the connection to break, the patient may injure his neck or face. A patient could quite possibly hang himself. Hence, fire codes and hospitals require easily detachable, pressure fit connectors.

Often, patients are unaware that they are no longer connected to a supply of oxygen. Several minutes after a patient starts to receive oxygen, his membranes dry, he grows accustomed to the nasal prongs, and he neither feels, nor notices, whether oxygen is flowing. Furthermore, a patient's medication may increase the likelihood that a problem will avoid detection until too late.

Often patients will sneeze, cough or expectorate secondary to illness and the use of oxygen. Typically, the oxygen delivery system will be intentionally turned off to monitor patient lung function with environmental air only. During either or both of these events, the oxygen tubing becomes a ready conduit through which the permanent oxygen delivery equipment becomes inoculated with germs.

Inventions aimed at alerting medical personnel of patients in distress have been the subject of earlier patents. Typically, the alert takes the form of an auditory cue.

U.S. Pat. No. 3,952,740, issued on Apr. 27, 1976, to James E. Scurlock, features an auditory cue. The Scurlock Patent discloses an alarm that sounds in response to a drop in oxygen pressure. Specifically, the device is a gas flow monitor for anesthetic machines. Should oxygen pressure fall too low, an electric switch sounds an alarm.

A whistle mechanism may be incorporated as a means of sounding an alarm. U.S. Pat. No. 4,350,647, issued on Sep. 21, 1982, to Exequile de la Cruz, discloses a permanent adapter for a medical humidifier. The adapter contains a valve. The valve opens in response to excessive oxygen pressure, producing an audible sound. The sound alerts medical personnel to the condition. Here, the source of the sound comes directly from the delivery system.

Other Patents considered to be of general relevance to the instant invention are those respectively granted and issued to Fowler et al. (GB 729,660), Rhodes (GB 765,847), G. E. Moore et al (U.S. Pat. No. 3,185,128), Black (U.S. Pat. No. 4,011,828), Williams (U.S. Pat. Nos. 4,215,646 and 4,215,646), Pasternack (U.S. Pat. No. 4,350,115), Olesen (U.S. Pat. No. 4,487,155), Chang (U.S. Pat. Nos. 4,745,877 and 4,793,190), Le Bec (U.S. Pat. No. 4,825,802), Hoffman (U.S. Pat. No. 5,057,822), Padula (U.S. Pat. No. 5,293,866) and Kloeppel (U.S. Pat. No. 5,865,174). Of particular note, U.S. Patents issued to Chang discloses rotary type flow indicators which produces fluid flow around flow bends.

None of the above inventions and patents, taken either singly or in combination, is seen to describe the instant invention as claimed.

SUMMARY OF THE INVENTION

The warning device according to the present invention is an oxygen delivery system which indicates failure of inadequate flow of oxygen. The device is placed in series between an oxygen source and a patient. A whistle mechanism is located at the distal end of the device. When pressure fitted tubing detaches from the device's distal end, the whistle sounds. The sound alerts those within earshot, that the oxygen delivery system has failed.

In addition, the device visually indicates that oxygen continues to flow. A clear acrylic ball, located at the device's centrist area, contains a fan. The fan is mounted so that it turns in response to oxygen flow. A turning fan indicates that oxygen is flowing. An anti-reflux valve is inserted proximally which will allow unobstructed fan rotation and subsequent air flow of oxygen, while reducing the risk of the oxygen tubing becoming a conduit for germs. A flexible self-closing membrane serves to prevent back flow of air.

Seeing the visual flow fan indicator turning, and not hearing the whistle alert, assures patent delivery of medical oxygen.

Accordingly, it is a principal object of the invention to provide a device which draws attention to oxygen delivery system failure.

It is another object of the invention to provide a visual clue to verify delivery of oxygen.

It is a further object of the invention for the system failure itself to create the auditory alert.

Further still, it is an object of the invention to secure the permanent equipment from repeated exposures to pathogens thereby limiting the nosocomial transmissions of pathogens.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
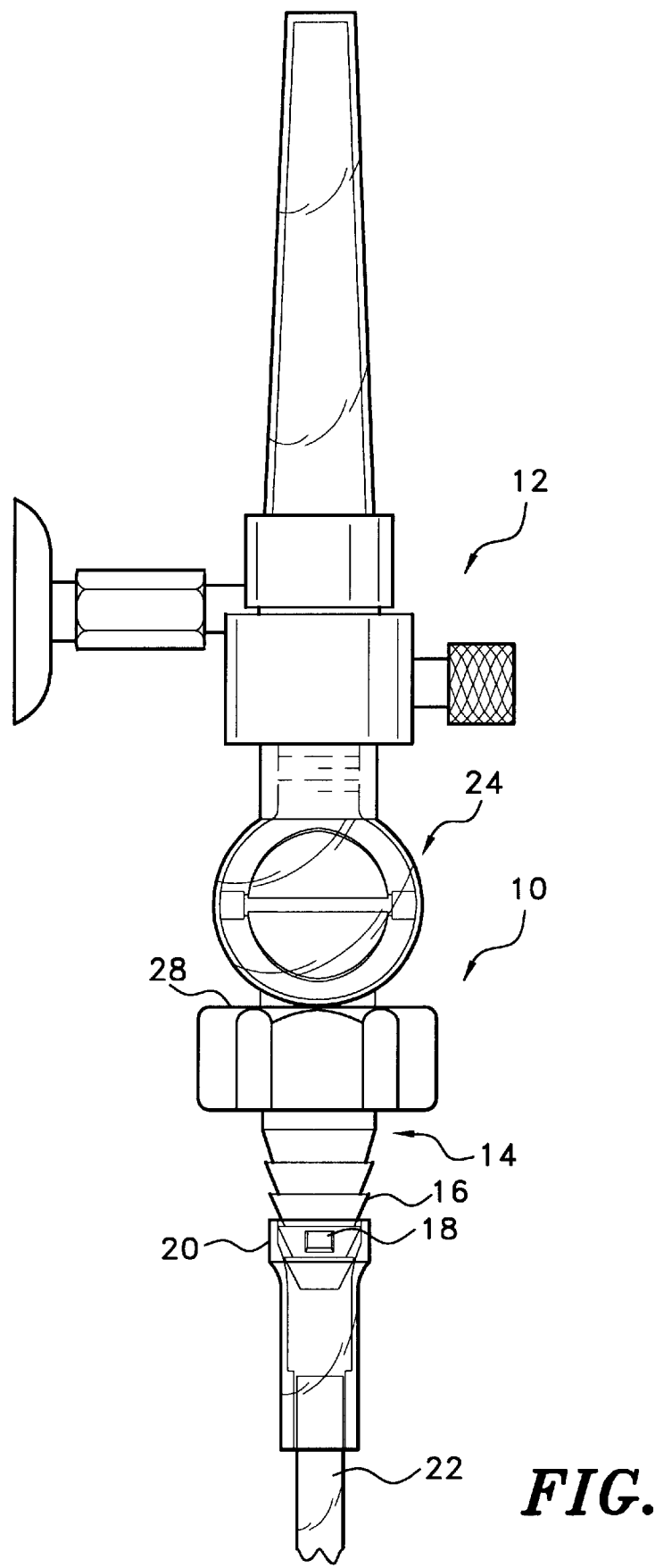
FIG. 1 is an environmental, perspective view of a warning device for oxygen delivery system failure according to the present invention.

The present invention relates to a warning device for oxygen delivery system failure. The device 10 sounds when a pressure fitted cannula coupler 20 detaches from the device's distal end 16. The device's proximal end 28 features a visual indicator 24 assuring an observer that oxygen continues to flow. Seeing a fan 32 within the visual indicator 24 turning, and not hearing the whistle alert, assures patent delivery of medical oxygen. The device 10 will first be discussed in reference to FIG. 1.

The device, designated generally as 10 in FIG. 1, attaches to an oxygen flow meter 12. In the U.S. and abroad, these meters are in standard use. However, the device 10 may be modified to accommodate other types of delivery systems. In this regard, the invention may incorporate a valve 23 (shown in FIG. 2, for reducing air flow reflux which includes a collapsible membrane 23a movably mounted therein which opens in the direction of air flow and closes in the presence of turbulent or similar back flow effects of air (See FIG. 2). The valve 23 is preferably substantially cylindrical in shape having a slightly tapered element 23b wherein, the body of the tapered element 23b has at least one tapered adjacent ridge 23c for abutment with an adapter end 24a of the visual indicator 24.

Figure 2:
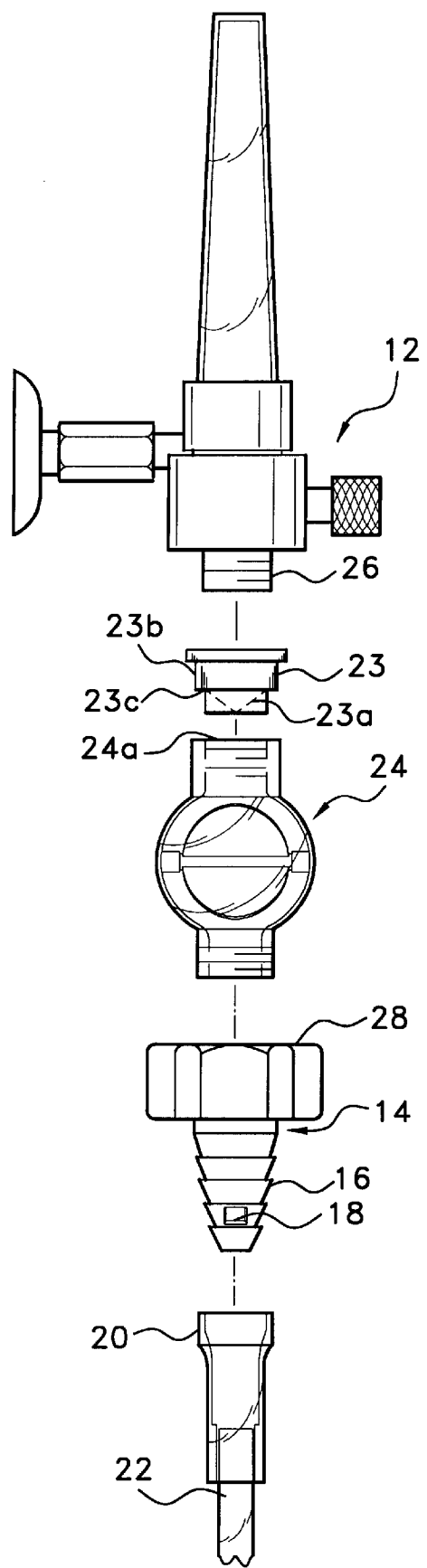
FIG. 2 is an exploded view of a warning device for oxygen delivery system failure according to the present invention.
Figure 4:
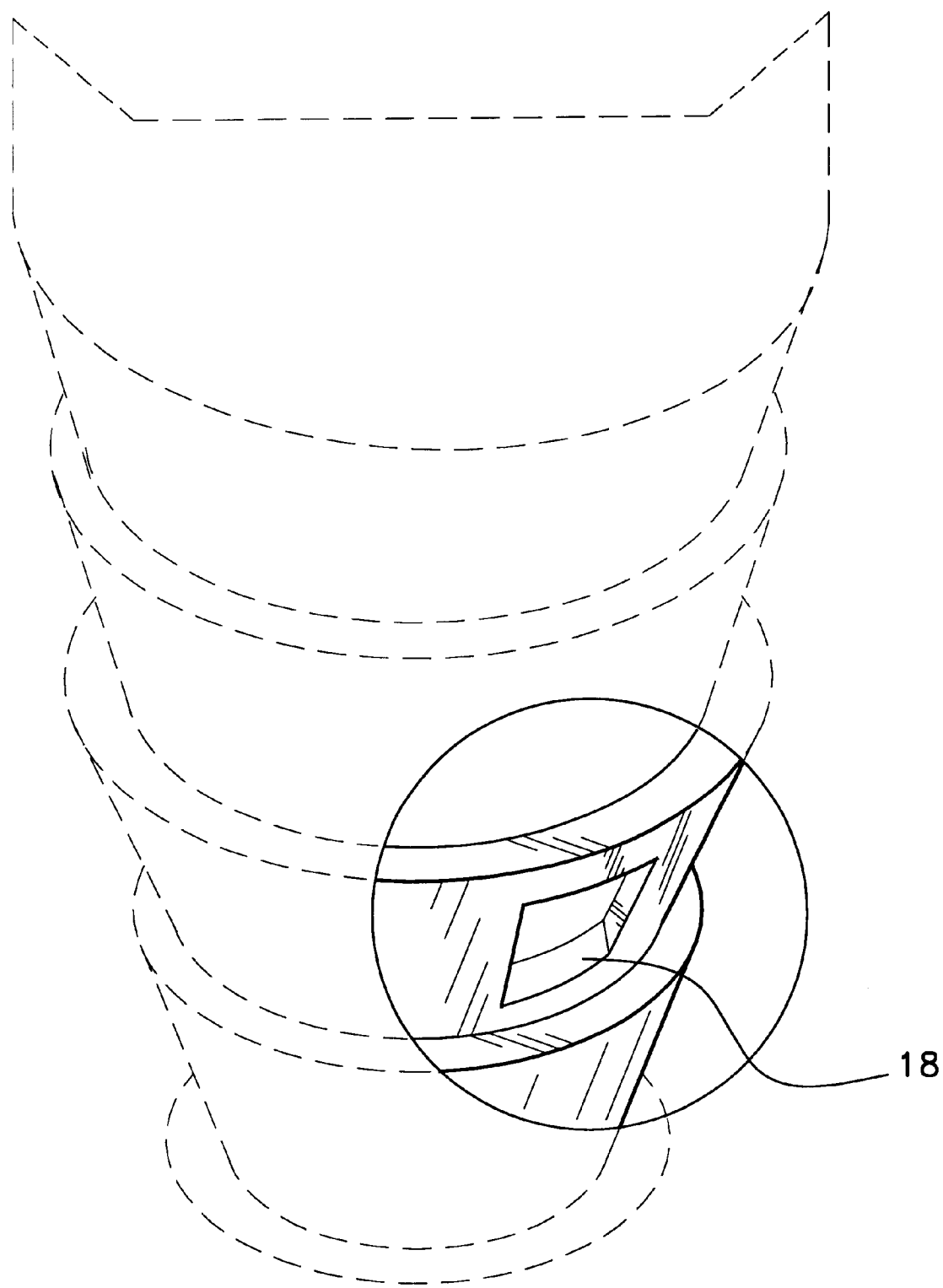
FIG. 4 is a detail of the area circled in FIG. 3.

A threaded "Christmas tree" coupler 14, with a whistle mechanism incorporated into its distal end 16, serves as the foundation for the device 10. In the preferred embodiment, the whistle mechanism is formed by the removal of material from the coupler's distal end 16. This creates an integrated reed 18. Referring to FIG. 4, one sees a close-up view of the reed 18. As seen in FIG. 1, a press-on, friction fit, malleable cannula coupler 20, covers the reed 18, preventing the device from making a sound. When, as illustrated in FIG. 2, the cannula coupler disconnects, the reed 18 is allowed to function, thereby producing an audible whistle. Those within earshot are alerted, and they may come to the aid of the patient.

Figure 5:
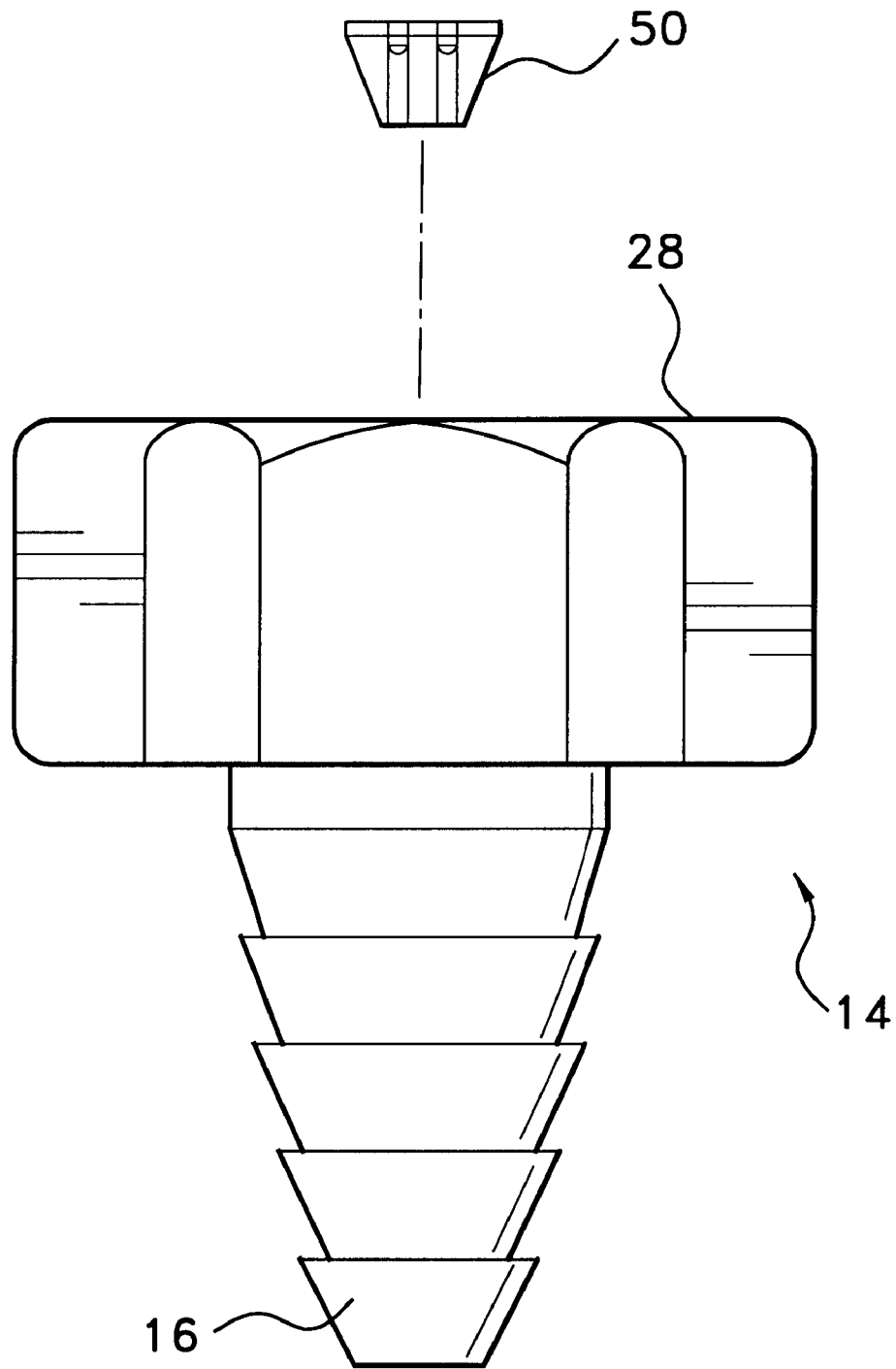
FIG. 5 illustrates an alternative embodiment of the invention having a drop-in whistle mechanism.

FIG. 5 features an alternative whistle mechanism 50. Here, the whistle mechanism is placed inside the Christmas tree coupler 14 by way of the coupler's proximal end 28. The inside of the coupler tapers, allowing the whistle 50 to be wedged inside, thereby preventing the whistle 50 from traveling through the Christmas tree coupler's distal end 16. When the cannula coupler 20 is attached, the tubing 22 sufficiently muffles the sound of the whistle 50. However, when the cannula coupler 20 detaches, the whistle sounds its warning. Although not featured in FIG. 5, a visual indicator 24 may be incorporated at the coupler's proximal end 28.

The visual indicator 24 is common to both embodiments. As seen in FIG. 1, the indicator 24 attaches to the Christmas Tree coupler's proximal end 28. The indicator 24 may be integrated into the Christmas tree coupler 14. In the alternative, the indicator maybe configured so that one attaches it in series with the flow meter's coupler port 26, and the Christmas tree coupler's distal end 28.

Figure 3:
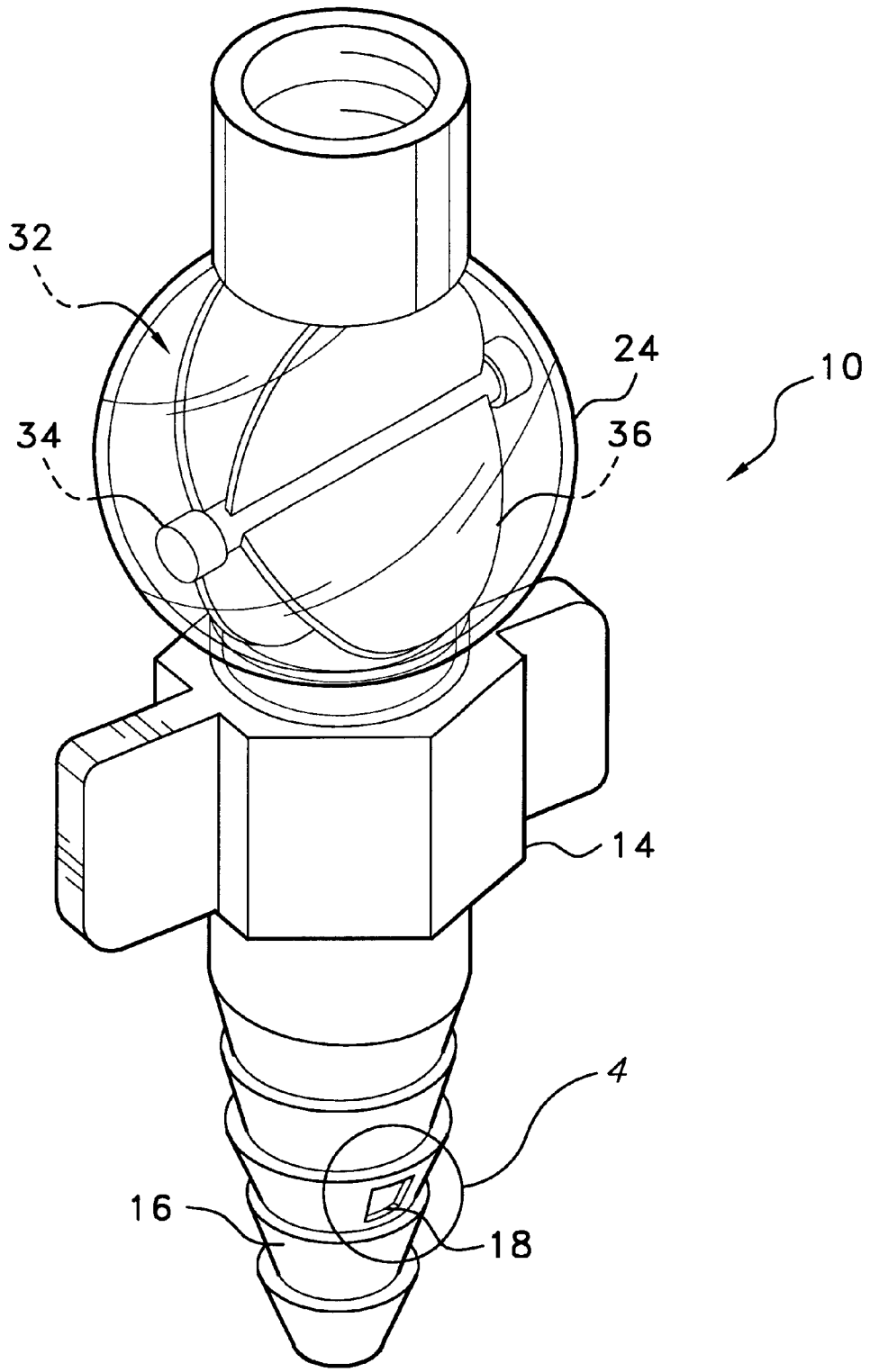
FIG. 3 is a front, perspective view of the device according to the present invention.

FIG. 3 illustrates a close-up of the visual indicator 24. The indicator 24 consists of transparent sphere 30 containing a fan 32. The fan's axle 34 is perpendicular to the flow of oxygen. The oxygen travels from the proximal end 28 to the distal end 16 of the Christmas tree coupler 14. Blades 36 extend radially from the fan's axle 34, and turn in response to the flow of oxygen. A turning fan indicates that oxygen is flowing. Other advantages of the invention include wherein the blades 36 of the fan include a pigment layer (i.e. dark green and light yellow) disposed on the outer surface to indicate the speed at which the fan 32 is turning, and subsequently the flow rate of oxygen therethrough. The fan 32 is preferably made of a light-weight material such as celluloid or similar material to provide minimal surface resistance for maximum air flow and rotation.

Figure 6:
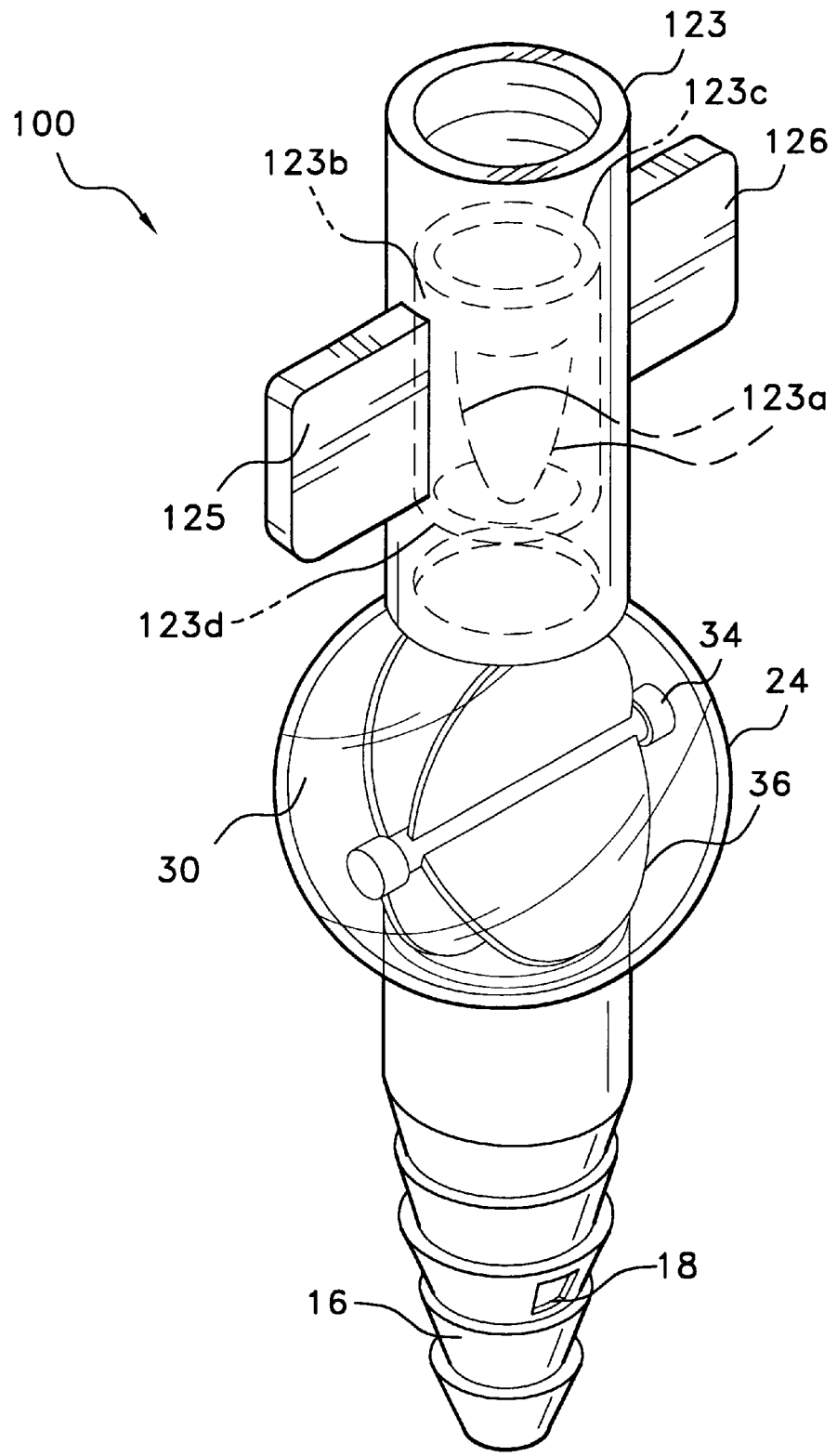
FIG. 6 is a perspective view of the warning device for oxygen delivery system failure, illustrating a single integrated anti-reflux valve unit.

As diagrammatically illustrated in FIG. 6, the device 10 is shown according to another embodiment 100, wherein the anti-reflux valve connector 123 is shown attached as an integral and permanent fixture of the device 10, identified in FIG. 1. The anti-reflux valve connector 123 having first and second support plates 125 and 126, respectively attaches to an oxygen flow meter 12 in a similar manner as diagrammatically illustrated in FIG. 2. Accordingly, the anti-reflux valve 123 further includes a collapsible membrane 123a movably mounted therein which opens in a direction of supplied air flow and closes in the presence of turbulent or similar back flow effects of air produced in a direction opposite supplied air flow (See FIG. 2). The anti-reflux valve 123 is preferably substantially cylindrical in shape having a central core 123b wherein, the body of the core element 123b has at least one recessed ridge 123a for fluid communication with an oxygen flow meter 12. A similar ridge 123d is made therein for fluid communication with an adapter end 24a of the visual indicator 24. As in the previous embodiment, a threaded "Christmas tree" coupler 14, with a whistle mechanism incorporated into its distal end 16, serves as the foundation for the device 10 and 123. Thus, the whistle mechanism is formed by the removal of material from the coupler's distal end 16. This creates an integrated reed 18.

Referring to FIG. 4 in comparison, one sees a close-up view of the reed 18. As seen in FIG. 1, a press-on, friction fit, malleable cannula coupler 20, covers the reed 18, preventing the device from making a sound. When, as illustrated in FIG. 2, the cannula coupler disconnects, the reed 18 is allowed to function, thereby producing an audible whistle in a usual manner. A professional care giver within earshot are alerted, and they may come to the aid of the patient.

It is understood that the present invention is not limited to the sole embodiments described above, but encompasses any and all embodiments within the scope of the following claims.

I claim:

1. A warning device for monitoring a connection in an oxygen delivery system, said warning device comprising:

a coupler having a conical distal end and a proximal end, said distal end being adapted for detachable connection to tubing that leads to a patient;

an indicator attached at the proximal end of said coupler, said indicator having an adaptor end for attachment to an oxygen source of the oxygen delivery system, said indicator including a transparent housing and a rotatable fan enclosed within the housing for visually indicating oxygen flow through the oxygen delivery system; and a whistle integrally disposed within the distal end of said coupler, whereby said whistle is prevented from producing an audible sound when connected to the tubing and emits an audible sound when the tubing becomes disconnected from the coupler.

2. The warning device according to claim 1, wherein said whistle consists of a reed opening integrally defined in the distal end of said coupler.

3. The warning device according to claim 1, wherein the adapter end of said indicator includes an anti-reflux valve for preventing back flow of air.

* * * * *